United States Patent

Nique et al.

[11] Patent Number: 5,679,788
[45] Date of Patent: Oct. 21, 1997

[54] 11 BETA-SUBSTITUTED-19 NOR-STEROIDS

[75] Inventors: Francois Nique, Le Perreux Sur Marne; Jean-Georges Teutsch, Pantin; Patrick Van de Velde, Paris, all of France

[73] Assignee: Roussel Uclaf, France

[21] Appl. No.: 731,561

[22] Filed: Oct. 16, 1996

Related U.S. Application Data

[62] Division of Ser. No. 512,284, Aug. 8, 1995, which is a division of Ser. No. 445,385, May 19, 1995, Pat. No. 5,556,845.

[30] Foreign Application Priority Data

Jun. 17, 1993 [FR] France ................... 93 07310

[51] Int. Cl.$^6$ ................... C07J 1/00; C07J 43/00
[52] U.S. Cl. ................... 540/95; 540/96; 552/626; 552/629; 552/646
[58] Field of Search ................... 552/626, 646, 552/629; 540/95, 96

[56] References Cited

U.S. PATENT DOCUMENTS

| | | | |
|---|---|---|---|
| 4,547,493 | 10/1985 | Teutsch et al. | 514/179 |
| 4,943,566 | 7/1990 | Nedelec et al. | 514/179 |
| 5,556,845 | 9/1996 | Nique et al. | 514/176 |

Primary Examiner—Jose G. Dees
Assistant Examiner—Barbara Badio
Attorney, Agent, or Firm—Bierman, Muserlian and Lucas

[57] ABSTRACT

Intermediate compounds of a formula selected from the group consisting of

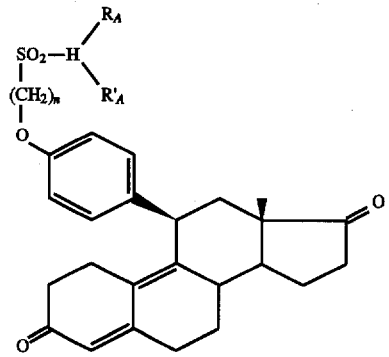

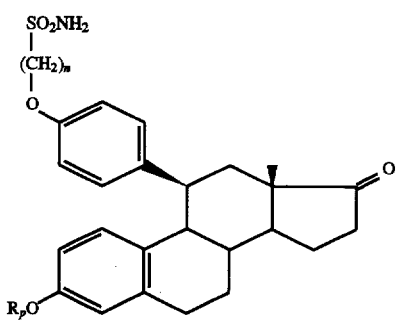

which are useful intermediates for the preparation of final products of the formula

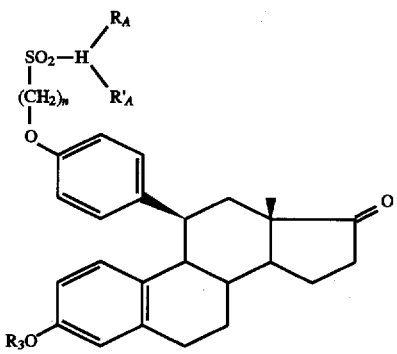

wherein the substituents are defined in the specification.

1 Claim, No Drawings

11 BETA-SUBSTITUTED-19 NOR-STEROIDS

PRIOR APPLICATIONS

This application is a division of U.S. patent application Ser. No. 512,284 filed Aug. 8, 1995 which is a division of U.S. patent application Ser. No. 445,385 filed May 19, 1994, now U.S. Pat. No. 5,494,907.

OBJECTS OF THE INVENTION

It is an object of the invention to provide the novel 19-nor steriods of formula I and their non-toxic, pharmaceutically acceptable salts and a process and intermediates for their preparation.

It is another object of the invention to provide anti-estrogenic compositions and a method of inducing anti-estrogenic activity in warm-blooded animals.

These and other objects and advantages of the invention will become obvious from the following detailed description.

THE INVENTION

The novel compounds of the invention are selected from the group consisting of a compound of the formula

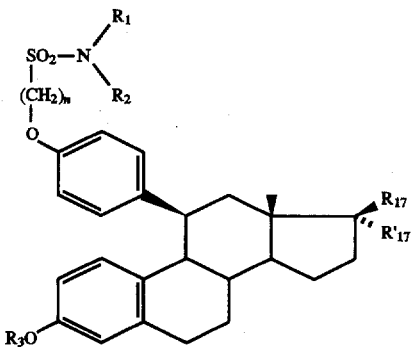

I wherein $R_{17}$ and $R'_{17}$ form =O or $R_{17}$ is —OH or acyloxy of an organic carboxylic acid of up to 12 carbon atoms and $R'_{17}$ is selected from the group consisting of hydrogen and alkyl, alkenyl and alkynyl of up to 8 carbon atoms, all optionally substituted with at least one member of the group consisting of halogen, —$NH_2$, optionally oxidized mono and di-alkylamino of 1 to 4 alkyl carbon atoms, amino alkyl of 1 to 6 carbon atoms, dialkylamino alkyl, dialkylamino-alkoxy, free or salified carboxy, carboxy esterified with lower alkyl, alkyl of 1 to 8 carbon atoms optionally substituted with at least one halogen, acyl and acyloxy of an organic carboxylic acid of up to 6 carbon atoms, OH, =O, —CN, —$NO_2$, formyl, alkoxy and alkylthio of 1 to 8 carbon atoms, carbamoyl, alkenyl and alkynyl of up to 8 carbon atoms, phenyl, furyl and thienyl, $R_3$ is selected from the group consisting of hydrogen, alkyl and cycloalkyl of up to 8 carbon atoms, acyl of an organic carboxylic acid of up to 12 carbon atoms and $R_1$ and $R_2$ are individually selected from hydrogen, alkyl and cycloalkyl of up to 8 carbon atoms optionally substituted, an acyl radical of an organic carboxylic acid of up to 12 carbon atoms and aryl and aralkyl of 1 to 6 alkyl carbon atoms and the aryl is mono or polycyclic optionally containing at least one heteroatom of sulfur, oxygen or nitrogen, $R_2$ is hydrogen and $R_1$ is selected from the group consisting of carbamoyl monosubstituted by alkyl or cycloalkyl of up to 8 carbon atoms optionally substituted or aryl or aralkyl defined as above or $R_1$ and $R_2$ form a dialkylamino methylene of 1 to 4 alkyl carbon atoms or $R_1$ and $R_2$ together with the nitrogen to which they are attached form a saturated heterocycle of 5 to 6 ring members optionally containing a heteroatom of sulfur, nitrogen or oxygen optionally substituted with alkyl of 1 to 4 carbon atoms or =O, n is an integer of 1 to 18 and their non-toxic, pharmaceutically acceptable addition salts with bases and acids.

Examples of acyloxy of an organic carboxylic acid of up to 12 carbon atoms are saturated or unsaturated aliphatic and cycloaliphatic carboxylic acids such as an alkanoic acid like acetic acid, propionic acid, butyric acid or isobutyric acid, valeric acid or undecylic acid; a hydroxyalkanoic acid such as hydroxyacetic acid, a cycloalkylcarboxylic or cycloalkylalkanoic acid such as cyclopropyl carboxylic acid, cyclopentyl carboxylic acid or cyclohexylcarboxylic acid, cyclopentyl or cyclohexyl acetic acid or propionic acid, benzoic acid, salicylic acid or a phenylalkanoic acid such as phenyl acetic acid or phenyl propionic acid, an amino acid such as diethylamino acetic acid or aspartic acid, formic acid or an optionally salified di-carboxylic acid such as butanedioic acid or the monosodium salt of the latter. It is preferably a derivative of acetic acid, propionic acid or butyric acid. By acyl is meant the group corresponding to the preceding acyloxy groups.

Alkyl of 1 to 6 carbon atoms may be methyl, ethyl, propyl, isopropyl, butyl, isobutyl, tert-butyl, n-pentyl, n-hexyl, 2-methyl pentyl, 2,3-dimethyl butyl, n-heptyl, 2-methylhexyl, 2,2-dimethylpentyl, 3,3-dimethyl pentyl, 3-ethylpentyl, n-octyl, 2,2-dimethylhexyl, 3,3-dimethylhexyl and 3-methyl-3-ethylpentyl and preferably methyl, ethyl, propyl or butyl.

Examples of cycloalkyl are cyclopropyl, cyclobutyl, cyclopentyl or cyclohexyl, preferably cyclopentyl.

When $R'_{17}$ is alkenyl, it may be vinyl, propenyl, isopropenyl, allyl, 2-methylallyl, butenyl or isobutenyl, preferably vinyl or propenyl When $R'_{17}$ is alkynyl, it may be the ethynyl, propynyl, propargyl, butynyl or isobutynyl, preferably ethynyl or propynyl.

Examples of mono or polycyclic aryl or aralkyl are carbocyclic monocyclic such as phenyl; a heterocyclic monocyclic such as thienyl, furyl, pyranyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, tetrazolyl, as well as the position isomers of the heteroatom or heteroatoms which contain; a carbocyclic condensed ring, for example naphthyl or phenanthrenyl, a heterocyclic condensed ring, for example benzofuranyl, benzothienyl, benzimidazolyl, benzothiazolyl, naphtho[2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl, imidazopyridyl, imidazopyrimidinyl or the condensed polycyclic systems constituted by heterocyclic monocyclics as defined above such as furo[2,3-b]pyrrole or thieno[2,3-b]furan, and more particularly phenyl, furyl such as 2-furyl, imidazolyl such as 2-imidazolyl, pyridyl such as 2-pyridyl, 3-pyridyl, 4-pyridyl, pyrimidinyl such as pyrimid-2-yl, thiazolyl such as thiazol-2-yl, thiazolinyl such as thiazolin-2-yl, triazolyl such as triazol-2-yl, tetrazolyl such as tetrazol-2-yl, benzimidazolyl such as benzimidazol-2-yl, benzothiazolyl such as benzothiazol-2-yl, purinyl such as purin-7-yl or quinolyl such as 4-quinolyl, and an example of an aralkyl is methyl or ethyl substituted by one of the above aryls.

Examples of saturated nitrogenous heterocycle with 5 or 6 members optionally containing a second heteroatom chosen from nitrogen, oxygen and sulfur and optionally substituted by an alkyl or by carbonyl, is preferably pyrrolidine, piperidine, piperazine, morpholine, thiamorpholine or imidazolidinone.

The optional substituents of the different groups above are preferably selected from the group consisting of halogen such as fluorine, chlorine, bromine or iodine, amino, alkylamino such as methylamino or ethylamino, dialkylamino such as dimethylamino, diethylamino, methylethylamino, each of these dialkylamino optionally being in oxidized form, aminoalkyl such as aminomethyl or aminoethyl, dialkylaminoalkyl such as dimethylamino methyl or ethyl, dialkylaminoalkyloxy such as dimethylamino ethyloxy, hydroxyl, free, esterified carboxy such as alkoxycarbonyl, such as methoxycarbonyl or ethoxycarbonyl, or carboxy salified for example by a sodium or potassium, alkyl of 1 to 8 carbon atoms such as methyl, ethyl propyl, isopropyl, butyl, isobutyl, tert-butyl optionally substituted by at least one halogen, for example fluorine such as trifluoromethyl, oxo, cyano, nitro, formyl, acyl such as acetyl, propionyl, butyryl, benzoyl, acyloxy such as acetoxy or —O—CO—$(CH_2)_n CO_2H$ in which n=1 to 5, alkoxy such as methoxy, ethoxy, propyloxy, isopropyloxy, butyloxy, alkylthio such as methylthio, ethylthio, propylthio, isopropylthio, butylthio, carbamoyl, alkenyl such as vinyl, propenyl, alkynyl such as ethynyl, propynyl and aryl such as phenyl, furyl, thienyl.

As an example of such substituted groups are alkyl substituted by one or more halogen atoms, for example fluorine, such as trifluoromethyl, trifluorobutyl, pentafluoropropyl, pentafluorobutyl, pentafluoropentyl, heptafluorobutyl or nonafluorobutyl radical, or for example chlorine such as 2-chloroethyl. There can also be mentioned for example an aryl substituted by one or more halogens, for example chlorine such as 4-chlorophenyl.

Examples of suitable acids to form the acid addition salts when the compounds of formula I have an amino group are inorganic acids such as hydrochloric acid, hydrobromic acid, sulfuric acid, nitric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids such as methane sulfuric acid or ethane sulfonic acid, arylsulfonic acids, such as benzene or p-toluene sulfonic acid and arylcarboxylic acids and when the compounds of formula I contain an acid function, examples of bases are salts of alkali or alkaline-earth metals or of optionally substituted ammonium.

A preferred group of compounds are those of the formula

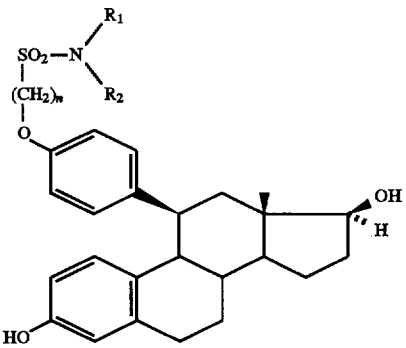

I' wherein $R_1$ and $R_2$ are individually selected from the group consisting of hydrogen, alkyl and cyclic alkyl of up to 8 carbon atoms optionally substituted, an acyl of an organic carboxylic acid of up to 12 carbon atoms, or optionally substituted phenyl, or $R_1$ is carbamoyl monosubstituted by an optionally substituted alkyl or cyclic alkyl of up to 8 carbon atoms, or by optionally substituted phenyl, and $R_2$ is hydrogen, or $R_1$ and $R_2$ form with the nitrogen atom to which they are linked a cyclic urea of the formula

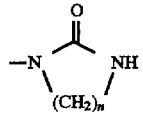

n' being 2 or 3, or $R_1$ and $R_2$ form a dimethylaminomethylene and n is 1 to 7, as well as the addition salts thereof.

Among the preferred compounds of formula I are those wherein $R_{17}$ is —OH and $R'_{17}$ is hydrogen, those wherein n is 5 or 6, those wherein $R_1$ and $R_2$ are hydrogen or alkyl or cycloalkyl of up to 8 carbon atoms optionally substituted with at least one halogen, those wherein $R_1$ is hydrogen and $R_2$ is alkyl or cycloalkyl of up to 8 carbon atoms, those wherein $R_2$ is hydrogen and $R_1$ is carbamoyl monosubstituted with alkyl or cycloalkyl of up to 8 carbon atoms or phenyl, all optionally substituted with at least one halogen.

Specific preferred compounds of formula I are N-butyl-5-[4-($\Delta$1,3,5(10)-estratrien-3,17β-diol-11β-yl)-phenoxy]-pentane-sulfonamide, N-butyl 5-[4-($\Delta$1,3,5(10)-estratrien-3,17β-diol-11β-yl)-phenoxy]-N-methyl-pentanesulfonamide and 5-[4-($\Delta$1,3,5(10)-estratrien-3,17β-diol-11β-yl)-phenoxy]-N-(2,2,3,3,4,4,4-heptafluorobutyl)-N-methyl-pentanesulfonamide.

The process for the preparation for the compounds of formula I comprises reacting a compound of the formula

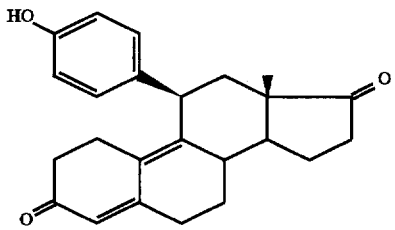

II in which the phenol function is optionally protected,

A) either with a halogenated derivative of the formula

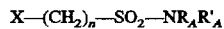

III in which X is halogen, n has the above meaning $R_A$ and $R'_A$ are individually selected from the group consisting of hydrogen, optionally substituted alkyl, acyl of an organic carboxylic acid, optionally substituted aryl or aralkyl with at least one of $R_A$ and $R'_A$ not being hydrogen or form with the nitrogen to which they are attached a saturated nitrogenous heterocycle with 5 or 6 ring members optionally containing a second heteroatom selected from nitrogen, oxygen and sulfur and optionally substituted by alkyl to obtain a compound of the formula

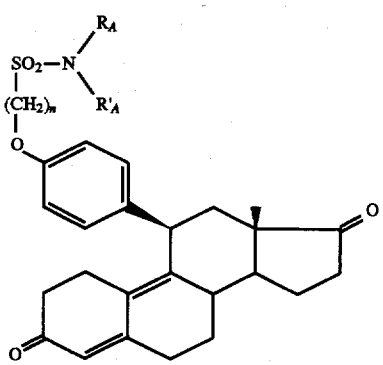

in which n, $R_A$ and $R'_A$ have the same meaning, subjecting the latter to the action of an aromatization agent of ring A, and optionally of an acylation agent of the 3-hydroxyl to obtain a product of the formula

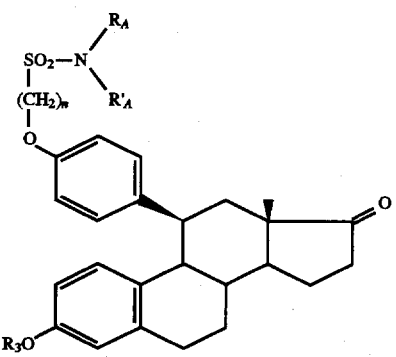

and in which n, $R_A$ and $R'_A$ have the above meaning and $R_3$ is hydrogen or an acyl, optionally subjecting the latter if necessary to one or more of the following reactions, in any appropriate order:
reduction of the 17-ketone function
addition on the 17-ketone function of a metal complex of the formula

      X in which M is a metal and $R'_{17a}$ has the same meaning as $R'_{17}$ with the exception of hydrogen,
selective acylation in position 17 when $R_{17}$ is hydroxyl, alkylation or acylation of the 3-hydroxyl,
saponification when $R_3$ is acyl, optional salification by an acid or a base,
B) or to the action of an aromatization agent of the A ring and to a protection reaction of the 3-hydroxyl, then to a selective elimination reaction of the protective group of the 11-phenol to obtain a product of the formula

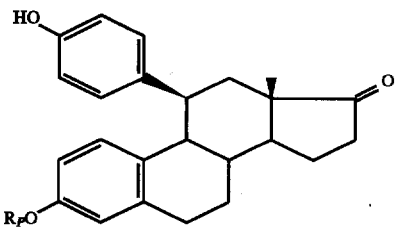

in which Rp is a protective group, subjecting the latter to the action of a compound of the formula

      III

X is halogen, $Alk_1$ and $Alk_2$ are alkyl of 1 to 4 carbon atoms and n is 1 to 18, then to a hydrolysis reaction of the imine formed to obtain a compound of the formula

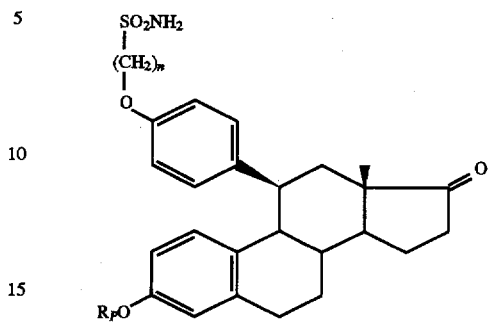

in which n and Rp have the above meaning, being able if appropriate according to the nature of Rp, to correspond to a product of formula I, which product of formula VI is optionally subjected and if necessary to one or more of following reactions in any appropriate order:

elimination reaction of the Rp protective group reduction of the 17-ketone function addition on the 17-ketone function of a metal complex of the formula

      X as defined previously, selective acylation in position 17 when $R_{17}$ is hydroxyl alkylation or acylation of the 3-hydroxyl action of a halide of the formula

      VII in which $R_8$ is an optionally substituted alkyl or acyl and X is halogen to obtain a compound of the formula

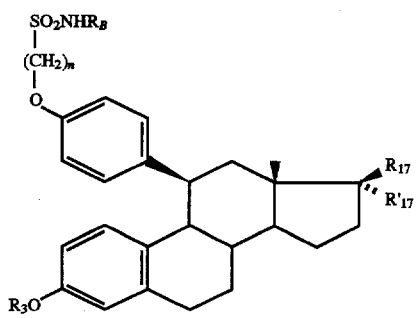

in which n, $R_{17}$, $R'_{17}$ and $R_3$ have the above meanings action of an isocyanate of the formula

      VIII in which $R_c$ is alkyl, aryl or aralkyl, each being optionally substituted to obtain the compound of the formula

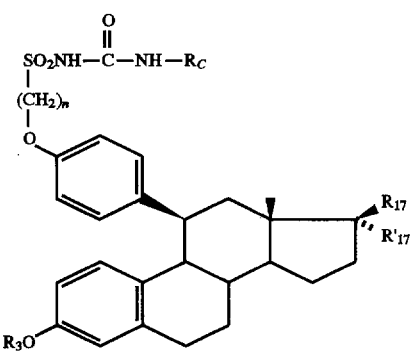

in which n, $R_{17}$, $R'_{17}$ and $R_3$ have the above meanings action of a compound of the formula $$(Alk_3O)(Alk_4O)CH-N(Alk_1)(Alk_2) \quad IX$$

in which $Alk_1$, $Alk_2$, $Alk_3$ and $Alk_4$ are alkyl of 1 to 4 carbon atoms to obtain a compound of the formula

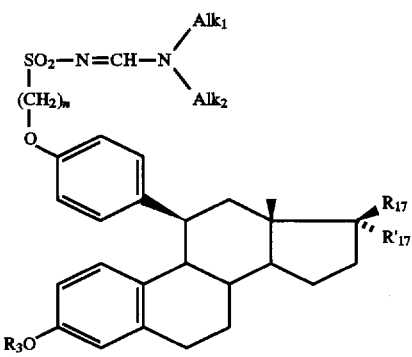

in which n, $R_{17}$, $R'_{17}$ and $R_3$ have the above meanings alkylation or acylation of the action of formula $I_B$ by the action of a halide of formula VII to obtain a corresponding dialkylated, diacylated or alkylacylated sulfonamide, cyclization reaction of the product of formula $I_C$ when $R_C$ is $(CH_2)_n$'-Hal, n' being 2 or 3 and Hal is halogen to obtain the product of formula $I'_C$ in which $R_1$ and $R_2$ form with the nitrogen to which they are linked a cyclic urea of the type:

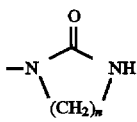

optional salification by an acid or a base.

The compounds of formula $I_A$, corresponding to the compounds of formula I in which $R_1=R_A$ and $R_2=R'_A$, are obtained by reacting a compound of formula II successively with a) a compound of formula III in the presence of a strong base such as sodium hydride in an aprotic dipolar solvent such as dimethylformamide operating, for example, at ambient temperature to obtain the intermediate compound of formula IV, b) an aromatization agent such as an acetyl bromide—acetic anhydride mixture followed by a saponification reaction carried out in the presence of potassium hydroxide in methanol or sodium hydroxide in methanol.

The compounds of formula VI are obtained by reacting a compound of formula II in which the 11-phenol is optionally protected successively with a) an aromatization agent such as palladium hydroxide on magnesia in methanol, followed by a protection reaction of the 3-hydroxy by the action for example of benzyl chloride in the presence of potassium carbonate in acetone operating under reflux for 7 hours, and followed by a selective deprotection reaction of the 11-phenol, by a saponification carried out in the presence of potassium hydroxide in methanol or sodium hydroxide in methanol to obtain the intermediate compound of formula V, b) a compound of formula III' in the presence of a strong base such as sodium hydride in an aprotic dipolar solvent such as dimethylformamide, c) an acid hydrolysis agent of the imine formed in the preceding stage such as hydrochloric acid in a methanol—tetrahydrofuran mixture.

The compounds of formula $I_B$ are obtained by reacting a compound of formula VI, in which $OR_p$ is a hydroxyl protected by aralkyl with a compound of formula VII, the reaction being carried out in the presence of sodium hydroxide in acetone under reflux or in the presence of sodium hydride in dimethyl-formamide at ambient temperature. A second alkylation or acylation can be carried out under the same operating conditions.

The compounds of formula $I_C$ are obtained by reacting a compound of formula VI, in which the protective group of the 3-hydroxyl is eliminated and the 17-ketone is reduced with a compound of formula VIII operating in the presence of a strong base such as sodium hydride in an aprotic dipolar solvent such as dimethyl-formamide operating, for example, at ambient temperature. When $R_C$ is of the $(CH_2)_n$'-Hal type, n' being 2 or 3, a cyclization reaction is produced in situ, the medium being very basic to form the compounds of formula $I'_C$.

The compounds of formula $I_D$ are obtained by reacting a compound of formula VI, in which the protective group of the 3-hydroxyl is eliminated and the 17-ketone is reduced, with a compound of formula IX, operating for example in dimethylformamide at ambient temperature.

When the compound of formula I contains a 17-ketone, the following are obtained:

the corresponding 17β-hydroxylated compound, for example by the action of a reducing agent such as sodium borohydride in a neutral solvent such as methanol, the corresponding compound containing an $R'_{17}$ being alkyl alkenyl or alkynyl optionally substituted by the addition of a compound X such as a lithium complex according to the process described in the European Patent EP No. 57,115.

It is well understood that if $R'_{17}$ is alkyl alkenyl or alkynyl optionally substituted by a reactive function, this may be provisionally protected by the usual methods.

When the compound of formula I possesses a 3-hydroxyl, the corresponding alkylated steroid is obtained by the action of an alkylation reagent such as alkyl iodide or alkyl sulfate for example methyl sulfate, or the corresponding acylated steroid is obtained by the action of a standard acylation agent such as an acyl halide such as acetyl chloride.

When the compound of formula I possesses a 17β-hydroxyl, the corresponding acyloxylated 17β steroid is obtained by the action of a selective acylation agent, for example acetic anhydride in pyridine optionally in the presence of 4-dimethylamino-pyridine, or any other way known to a man skilled in the art.

The protective groups that can be used to protect the reactive functions, such as the hydroxyl function, are chosen from the usual groups of organic chemistry and more particularly the chemistry of the peptides. A non-exhaustive list of these groups as well as the corresponding elimination methods will be found in French Patent No. 2,499,995 whose content is incorporated by reference, as well as in the following work: Protective group in organic synthesis (GREENE and WUTS (1991) Ed. WILEY).

The acetyl, benzoyl or terbutyldimethylsilyl can be mentioned for example for the protection of the 11-phenol of the compound of formula II. The acetyl, benzoyl or benzyl can be mentioned for example for the protection of the 3-hydroxyl of the compounds of formulae V and VI.

For example, the protection reaction of the 3-hydroxyl with benzyl can be carried out by the action of benzyl chloride in the presence of a strong base such as sodium hydride in a dipolar aprotic solvent such as dimethylformamide at ambient temperature, or by the action of benzyl bromide in the presence of a weaker base such as potassium carbonate in acetone under reflux. This protection is useful because it is resistant to hydrolysis or saponification reactions.

When the intermediate compounds contain protected reactive functions, the corresponding deprotected compound is obtained by the action of the usual agents. A non-exhaustive list of these groups as well as the corresponding elimination methods will be found in French Patent No. 2,499,995 whose content is incorporated in by reference, as well as in the following work: Protective group in organic synthesis (GREENE and WUTS (1991) Ed. WILEY).

Purely by way of indication, when the phenol is protected by acetyl, the elimination reaction of this protective group could be carried out using a saponification agent such as potassium hydroxide in alcoholic medium. When the phenol is protected by a terbutyldimethylsilyl group, the elimination reaction of this protective group could be carried out using a hydrolysis agent such as hydrochloric acid. When the 3-hydroxy is protected by benzyl, the elimination reaction of this protective group could be carried out preferably by hydrogenolysis by the action of hydrogen in the presence of a palladium catalyst on activated charcoal in an ethyl acetate/ethanol/acetic acid mixture.

In a preferred embodiment of the invention: the compounds of formula III are used in which X is preferably iodine, the compounds of formula III' are used in which X is preferably iodine, the compounds of formula VII are used in which X is preferably iodine in the case where $R_8$ is alkyl, and chlorine in the case where $R_8$ is acyl.

The invention also extends to a process as defined above, characterized in that at the start a compound is used corresponding to a compound of formula II containing in position 17, the $R_{17}$ and $R'_{17}$ substituents as defined above.

It goes without saying that in the implementation of such a process and as has already been mentioned for $R'_{17}$, intermediate protection of the $R_{17}$ and R'17 may be necessary. This protection is as defined above. The above starting products are known, for example, from published European Application No. 0,384,482, or are prepared by the processes described in the Application, from 17-oxo steroids.

The novel anti-estrogenic compositions of the invention are comprised of an anti-estrogenically effective amount of at least one compound of formula I and its non-toxic, pharmaceutically acceptable salts and an inert pharmaceutical carrier. The compositions may be in the form of tablets, dragees, capsules, granules, suppositories, pessaries, ointments, creams, gels, microspheres, implants, patches and injectable solutions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions of the invention also possess glucocorticoid or antiglucocorticoid, progestomimetic or antiprogestomimetic, androgen or anti-androgen, antimineralocorticoid, estrogen or anti-estrogen activities. The compositions possess in particular a remarkable anti-estrogenis activity and anti-proliferative properties as is shown by the tests given further on.

These properties make the compositions useful for combating the side effects of glucocorticoids. They also allow the combating of disorders due to a hypersecretion of glucocorticoids and notably ageing generally and more particularly hypertension, delay in healing, atherosclerosis, osteoporosis, diabetes, obesity as well as immunosuppresion and insomnia.

These compositions can also be used in the treatment of certain tumours which express the hormonal receptors for which the products of formula I have an affinity. The compositions which possess anti-progestomimetic properties can be used to prepare original contraceptives, as agents for interrupting pregnancy or as labour-inducing agents. These products can thus be used as period inducers for women and more generally for warm-blooded female animals.

The products are therefore administered during periods when progesterone plays an essential physiological role, that is to say during the luteal phase of the cycle, at the moment of nidation (or implantation of the embryo) and during pregnancy. A method of contraception of the invention consists of administering to the woman at least one of the products of formula I during 1 to 5 days preferably at the end of the cycle. This product is then preferably administered orally or in vagino but it can also be used parenterally. The products can also be used by endonasal route.

The products of formula I possessing anti-progestomimetic properties can also be used against hormonal disturbances and, furthermore, they can be useful in the treatment of hormone-dependent tumours. Their actions on the hypophyseal secretions make the products usable in menopause.

These products can also be used in the synchronization of oestrus and the synchronization of the dropping of young in farm animals, particularly bovines and ovines. The products can also be used to control the fertility of domestic animals such as dogs or cats.

The compounds of formula I can also have progestomimetic properties and can thus be used in the treatment of amenorrhea, dysmenorrhea and luteal insufficiencies.

The compounds of formula I which possess anti-androgen properties can be used in the treatment of hypertrophy and cancer of the prostate, virilism, anaemia, hirsutism and acne as well as for male contraception.

The compounds of formula I which possess estrogen properties are also usable in the treatment of disorders linked to a hypofolliculinemia, for example amenorrhea, dysmenorrhea, repeated miscarriages, premenstrual disorders, as well as in the treatment of the menopause and osteoporosis.

The anti-estrogen and anti-proliferative properties of the compounds of formula I make them useful in the treatment of hormone-dependent carcinomas such as breast carcinomas and their metastases and in the treatment of benign breast tumours.

The novel method of inducing anti-estrogenic activity in warm-blooded animals, including humans, comprises administering to warm-blooded animals an anti-estrogenically effective amount of at least one compound of formula I and its non-toxic, pharmaceutically acceptable salts. The compound may be administered orally, rectally, parenterally or topically. The usual effective daily dose is to mg/kg depending on the condition treated, the compound and method of administration.

The compounds of formulae IV, V and VI are new intermediate products and among the new intermediate products of the invention are N-butyl-5-[4-(Δ4,9-estradien-3,17-dione-11β-yl)-phenoxy]-N-methyl-pentanesulfonamide, 5-[4-(Δ4,9-estradien-3,17-dione-11β-yl)-phenoxy]-N-(2,2,3,3,4,4,4-heptafluorobutyl)-N-methyl-pentanesulfonamide, 11β-(4-hydroxyphenyl)-3-[benzyl-oxy]-Δ1,3,5(10)-estratrien-17-one and 5-[4-[17-oxo-3-[benzyl-oxy]-Δ1,3,5(10)-estratrien-11β-yl]phenoxy]-pentanesulfonamide.

The compound of formula II necessary for the implementation of the process is described in European Patent Application No. 0,384,842 (preparation of Example 43). Examples of the preparation of products of formulae III and III' appear in the experimental part. These compounds are generally known, and are prepared by similar processes to those described in the experimental part.

In the following examples, there are described several preferred embodiments to illustrate the invention. However, it should be understood that the invention is not intended to be limited to the specific embodiments.

PREPARATION 1

N-[dimethylaminomethylene]-5-iodo-pentane-sulfonamide

STEP A: 5-Chloropentane-sulfonamide 2.5 ml of a 28% aqueous solution of ammonium hydroxide were added dropwise at 0° to +5° C. under an inert gas atmosphere to a solution of 2.5 g of 5-chloropentane sulfonyl chloride (preparation described in: Bull. Soc. Chim. Belg. (1965) Vol. 74, p. 21) in 30 ml of tetrahydrofuran. The temperature was allowed to rise from 3° C. to 16° C., and the mixture was stirred at ambient temperature for 2 hours. The tetrahydrofuran was evaporated under reduced pressure and the residue was taken up in water, extracted with methylene chloride, washed with water, then with an aqueous solution of sodium chloride, dried and evaporated under reduced pressure to obtain 2.01 g of the expected product melting at 62° C.

IR Spectrum: Trichloromethane ($CHCl_3$)

| | |
|---|---|
| —$NH_2$ | 3448 $cm^{-1}$ |
| | 3352 $cm^{-1}$ |
| —$SO_2$— | 1344 $cm^{-1}$ |
| | 1150 $cm^{-1}$ |
| —$NH_2$ | 1545 $cm^{-1}$ |

STEP B: 5-chloro-N-[dimethylamino-methylene]-pentane-sulfonamide 1.29 ml of N,N-dimethylformamide-dimethyl acetal were added dropwise at ambient temperature under an inert gas atmosphere to a solution of 1.5 g of the product of Step A in 8 ml of dimethylformamide. The solution was stirred at ambient temperature for 3 hours, then poured into a 1% aqueous solution of sodium hydrogen sulfate, extracted with ethyl acetate, washed with water, then with a saturated aqueous solution of sodium chloride, dried and evaporated to dryness under reduced pressure to obtain 1.809 g of the expected product.

IR spectrum: ($CHCl_3$)

| | |
|---|---|
| —N=CH—N< | 1629 $cm^{-1}$ |
| —$SO_2$— | 1349 $cm^{-1}$ |
| | 1119 $cm^{-1}$ |

STEP C: N-[dimethylamino-methylene]-5-iodo-pentane-sulfonamide 2.98 g of sodium iodide were added to a solution of 2.09 g of the product of Step B in 31.5 ml of methyl ethyl ketone (M.E.K.), and the mixture was refluxed for 4 hours. After cooling, water was added and extraction was carried out with ethyl acetate. The extracts were washed with water, then with a saturated aqueous solution of sodium chloride, dried and evaporated to dryness under reduced pressure to obtain 2.69 g of the expected product.

IR Spectrum: ($CHCl_3$)

| | |
|---|---|
| —N=CH—N< | 1629 $cm^{-1}$ |

PREPARATION 2

N-butyl-5-iodo-N-methyl-pentanesulfonamide

STEP A: N-butyl-5-chloro-N-methyl-pentanesulfonamide 0.47 ml of N-butylmethylamine were added under an inert gas atmosphere to a solution of 410 mg of 5-chloropentane sulfonyl chloride in 10 ml of methylene chloride. The temperature rose from 13° C. to 26° C., and then after cooling to 0° to 5° C., 0.55 ml of triethylamine were added. The mixture was stirred at ambient temperature for 2 hours and the reaction medium was poured into an aqueous solution of 1M hydrochloric acid, extracted with methylene chloride, washed with water, then with a saturated aqueous solution of sodium chloride, dried and evaporated to dryness under reduced pressure to obtain 486 mg of the expected product.

IR Spectrum: ($CHCl_3$)

| | |
|---|---|
| —$SO_2$—N< | 1334 $cm^{-1}$, 1142 $cm^{-1}$ |

STEP B: N-butyl-5-iodo-N-methyl-pentanesulfonamide 526 mg of sodium iodide were added to a solution of 449 mg of the product of Step A in 4.5 ml of methyl ethyl ketone, and the mixture was stirred at reflux for 4 hours. After cooling, the methyl ethyl ketone was evaporated under reduced pressure and water was added. Extraction was carried out with ethyl acetate and the extracts were washed with water, then with a saturated aqueous solution of sodium chloride, dried and evaporated to dryness under reduced pressure to obtain 572 mg of the expected product.

IR Spectrum: ($CHCl_3$)

| | |
|---|---|
| —$SO_2$—N< | 1334 $cm^{-1}$, 1141 $cm^{-1}$ |

PREPARATION 3

N-(2,2,3,3,4,4,4-heptafluorobutyl)-5-iodo-N-methyl-pentanesulfonamide

STEP A: 5-chloro-N-(2,2,3,3,4,4,4-heptafluorobutyl)-N-methyl-pentanesulfonamide 500 mg of N-(2,2,3,3,4,4,4-heptafluorobutyl)-N- methylamine hydrochloride (obtained according to European Patent No. 384,842 Example 75) and then, at 0° to 5° C., 0.55 ml of triethylamine were added to a solution of 200 mg of 5-chloropentane sulfonyl chloride in 5 ml of methylene chloride, and the mixture was stirred at ambient temperature for 2 hours. Water was added and extraction was carried out with methylene chloride. The extracts were washed with water, then with a saturated aqueous solution of sodium chloride, dried and evaporated to dryness under reduced pressure to obtain 378 mg of the expected product.

IR Spectrum: ($CHCl_3$)

| | |
|---|---|
| —$SO_2$—N< | 1354 $cm^{-1}$, 1341 $cm^{-1}$, 1148 $cm^{-1}$ |
| Impurity C=O | 1730 $cm^{-1}$ |

STEP B: N-(2,2,3,3,4,4,4-heptafluorobutyl)-5-iodo-N-methyl-pentanesulfonamide 300 mg of sodium iodide were added to a solution of 355 mg of the product of Step A in 3 ml of methyl ethyl ketone and the mixture was refluxed for 4 hours. After evaporation of the solvent, the residue was taken up in water and extracted with ethyl acetate. The extracts were washed with an aqueous solution of sodium thiosulfate, then of sodium chloride, and evaporated to dryness under reduced pressure to obtain 425 mg of the expected product in the form of a colourless oil which slowly crystallized.

IR Spectrum: ($CHCl_3$)

| | |
|---|---|
| N—$SO_2$— | 1354 $cm^{-1}$, 1341 $cm^{-1}$, 1148 $cm^{-1}$ |

PREPARATION OF EXAMPLE 1

11β-(4-hydroxyphenyl)-3-[(benzyl-oxy]-1,3,5(10)-estratrien-17-one

STAGE A: 11β-[4-(benzoyloxy)-phenyl]-Δ4,9-estradiene-3,17-dione 3 ml of benzoyl chloride were added dropwise under an inert gas atmosphere at 0° to +5° C. to a solution of 8.758 g of 11β-(4-hydroxyphenyl)-Δ4,9-estradiene-3,17-dione (prepared by Example 43 of Patent EP No. 384,842) in 92 ml of acetone and 27 ml of 1M aqueous sodium hydroxide. At the end of the introduction of the benzoyl chloride, precipitation of the benzoate was observed and the suspension was stirred for 10 minutes in an ice bath, then for 30 minutes at ambient temperature. It was poured into an aqueous solution of 0.1M hydrochloric acid and extracted with ethyl acetate. The extracts were washed with a saturated aqueous solution of sodium chloride, dried and evaporated to dryness under reduced pressure to obtain 12.98 g of the crude product which was crystallized from a methylene chloride/isopropyl ether mixture to obtain 9.93 g of the desired product melting at 196° C.

IR Spectrum: ($CHCl_3$)

| | |
|---|---|
| >C=O in position 17 + ketone of Ar—O—CO—Ph: | 1736 $cm^{-1}$ (F) |
| conjugated ketone: | 1659 $cm^{-1}$ |
| | 1602 $cm^{-1}$ |
| Aromatic C=C's: | 1505 $cm^{-1}$ |
| | 1490 $cm^{-1}$ |

STEP B: 11β-[4-(benzoyloxy)-phenyl]-3-hydroxyΔ1,3,5(10)-estratrien-17-one 10.1 g of palladium hydroxide at 20% on magnesium oxide were added to a solution of 10.07 g of the product of Step A in 104 ml of methanol and the mixture was refluxed for 90 minutes. After cooling, the suspension was filtered and the insoluble catalyst was washed with a methylene chloride/methanol mixture 50/50. The filtrate was evaporated to dryness under reduced pressure and the 10.72 g of residue were chromatographed on silica (eluant:ethyl acetate/cyclohexane 40/60) to obtain 7.72 g of the desired product melting at 265° C.

IR spectrum: ($CHCl_3$)

| | |
|---|---|
| —OH: | 3599 $cm^{-1}$ |
| >C=O: | 1733 $cm^{-1}$ (F) |
| | 1611 $cm^{-1}$ |
| | 1602 $cm^{-1}$ |
| Aromatic C=C's: | 1585 $cm^{-1}$ |
| | 1508 $cm^{-1}$ |

STEP C: 11β-[4-(benzoyloxy)-phenyl]-3-[benzyl-oxy]-Δ1,3,5(10)-estratrien-17-one 3.82 g of potassium carbonate and 4.9 ml of benzyl bromide (Fluka A007832) were added to a solution of 6.462 g of the product of Step B in 110 ml of acetone and the mixture was refluxed for 7 hours. Then after cooling, the mixture was evaporated to dryness under reduced pressure and the residue was taken up in ethyl acetate and poured into an aqueous solution of 0.5M hydrochloric acid. Extraction was carried out with ethyl acetate and the extracts were washed with a saturated aqueous solution of sodium chloride, dried and evaporated to dryness under reduced pressure. The 12.2 g of residue were chromatographed on silica (eluant:ethyl acetate/cyclohexane 25/75) to obtain 6.68 g of the desired product.

IR Spectrum: ($CHCl_3$)

| | |
|---|---|
| >C=O: | 1734 $cm^{-1}$ complex |
| | 1604–1608 $cm^{-1}$ |
| | 1586 $cm^{-1}$ |
| Aromatic C=C's: | 1576 $cm^{-1}$ |
| | 1508 $cm^{-1}$ |
| | 1501 $cm^{-1}$ |

STEP D: 11β-(4-hydroxyphenyl )-3-[benzyl-oxy]Δ1,3,5(10)-estratrien-17-one 12 ml of an aqueous solution of 2M sodium hydroxide were added to a solution of 6.64 g of the product of Step C in 87.5 ml of methanol and 87.5 ml of tetrahydrofuran and the mixture was stirred for one hour at ambient temperature. The reaction mixture was poured into a 0.5M aqueous solution of hydrochloric acid and extraction was carried out with ethyl acetate. The extracts were washed with water, then with a saturated aqueous solution of sodium bicarbonate, then with a saturated aqueous solution of sodium chloride, dried and evaporated to dryness under reduced pressure to obtain 6.52 g of the expected crude product which was crystallized from methylene chloride to obtain 4.62 g of the desired product melting at 240° C.

IR Spectrum: ($CHCl_3$)

| | |
|---|---|
| —OH: | 3600 $cm^{-1}$ |
| >C=O: | 1733 $cm^{-1}$ |
| | 1613 $cm^{-1}$ |
| | 1594 $cm^{-1}$ |
| Aromatic C=C: | 1574 $cm^{-1}$ |
| | 1513 $cm^{-1}$ |
| | 1500 $cm^{-1}$ |

EXAMPLE 1

5-[4-(Δ, 1,3,5(10)-estratrien-3,17β-diol-11β-yl)phenoxy]-pentanesulfonamide

STEP A: N-[dimethylamino-methylene]-5-[4-[3-benzyl-oxy]-Δ1,3,5(10)-estratrien-17-one-11β-yl]-phenoxy]-pentanesulfonamide After stirring for 25 minutes, a solution of 2.67 g of the product of Preparation 1 (Stage C) in 25 ml of dimethylformamide was added under an inert gas atmosphere to a suspension of 2.92 g of the product of Step D of the preparation of Example 1 in 69 ml of dimethylformamide and 403 mg of sodium hydride at 50% in oil. The suspension was heated at 50° C. and after 10 minutes, a solution was obtained which was stirred at this temperature for 75 minutes. The solution was cooled to ambient temperature and poured into a 1% aqueous solution of sodium hydrogen sulfate and extracted with ethyl acetate. The extracts were washed with water, then with a saturated solution of sodium thiosulfate and with a saturated aqueous solution of sodium chloride, dried and evaporated to dryness under reduced pressure. The 6.75 g of residue were chromatographed on silica (eluant:ethyl acetate) to obtain 3.82 g of the desired product.

IR Spectrum: (CHCl$_3$)

| >C=O in position 17: | 1733 cm$^{-1}$ |
|---|---|
| —N=CH—: | 1629 cm$^{-1}$ |
| | 1611 cm$^{-1}$ (shoulder) |
| | 1575 cm$^{-1}$ |
| Aromatic C=C's: | 1512 cm$^{-1}$ |
| | 1500 cm$^{-1}$ |
| —SO$_2$—: | 1349 cm$^{-1}$ |

STEP B: 5-[4-[3-[benzyl-oxy]-Δ1,3,5(10)-estratrien-17-one-11β-yl]-phenoxy]-pentanesulfonamide.

17.7 ml of 22° Bé pure concentrated hydrochloric acid were added under an inert gas atmosphere, to a suspension of 3.818 g of the product of Step A in 59 ml of methanol and 28 ml of tetrahydrofuran. The mixture was heated to 80° C. for 90 minutes, and then, after cooling, it was poured into a saturated aqueous solution of sodium bicarbonate. Extraction was carried out with ethyl acetate and the extracts were washed with a saturated aqueous solution of sodium chloride, dried and evaporated to dryness under reduced pressure. The 4.15 g of residue was chromatographed on silica (eluant: ethyl acetate/cyclohexane 60/40) to obtain 2.89 g of desired product.

IR Spectrum: (CHCl$_3$)

| —NH$_2$ | 3444 cm$^{-1}$ |
|---|---|
| | 3350 cm$^{-1}$ |
| >C=O in position 17: | 1733 cm$^{-1}$ |
| | 1610 cm$^{-1}$ |
| Aromatic C=C's: + | 1580 cm$^{-1}$ |
| —NH$_2$: | 1545 cm$^{-1}$ |

STEP C: 5-[4-[3-[benzyl-oxy]-Δ1,3,5(10)-estratrien-17β-ol-11β-yl]-phenoxy]-pentanesulfonamide 169 mg of and sodium borohydride were added at 0° to +5° C. under an inert gas atmosphere to a solution of 1.36 g of the product of Step B in 6 ml of methanol and 6 ml of tetrahydrofuran. After stirring at 0° to +5° C. for one hour, the reaction mixture was poured into a 1M aqueous solution of hydrochloric acid and extracted with ethyl acetate. The extracts were washed with water, then with a saturated solution of sodium chloride, dried and evaporated to dryness under reduced pressure to obtain 1.299 g of the expected crude product which were crystallized from a methylene chloride/isopropyl ether mixture to obtain 1.295 g of the desired product melting at 146° C.

IR Spectrum: (CHCl$_3$)

| —OH: | 3609 cm$^{-1}$ |
|---|---|
| —NH$_2$: | 3444 cm$^{-1}$ |
| | 3353 cm$^{-1}$ |
| | 1609 cm$^{-1}$ |
| Aromatic C=C's: | 1580 cm$^{-1}$ |
| | 1512 cm$^{-1}$, 1500 cm$^{-1}$ |
| —NH$_2$: | 1544 cm$^{-1}$ |

STEP D: 5-[4-(Δ, 1,3,5(10)-estratrien-3,17β-diol-11β-yl)-phenoxy]-pentanesulfonamide 161 mg of 10% palladium on activated charcoal (type E 10N, Degussa) were added to a solution of 1.295 g of the product of Step C in 50 ml of ethanol and 5 ml of acetic acid and then the mixture was stirred under a hydrogen pressure of 1640 mbar for 2 hours. After filtering, washing was carried out with a methanol/methylene chloride mixture 1/1, followed by evaporating to dryness under reduced pressure. The acetic acid was removed by entraining with toluene to obtain 1.04 g of the expected crude product which was crystallized from ethanol to obtain 736 mg of the desired product melting at 175° C.

IR Spectrum: (Nujol)

| Complex absorption OH/NH region | 1616 cm$^{-1}$ |
|---|---|
| Aromatic C=C's: | 1580 cm$^{-1}$ |
| + —NH$_2$ | 1511 cm$^{-1}$ |
| —SO$_2$ | 1333 cm$^{-1}$ |
| | 1153 cm$^{-1}$ |

EXAMPLE 2

N-butyl-5-[4-(Δ, 1,3,5(10)-estratrien-3,17β-diol-11β-yl)-phenoxy]-pentanesulfonamide STEP A: N-butyl-5-[4-[benzyl-oxy]-Δ1,3,5(10)-estratrien-17-one-11β-yl]-phenoxy]-pentanesulfonamide 0.188 ml of 1-iodobutane was added under an inert gas atmosphere to a solution of 500 mg of the product of Step B of Example 1 in 6.5 ml of acetone and 0.96 ml of a 1M aqueous solution of sodium hydroxide and the mixture was stirred at reflux for 52 hours. Then, the mixture was cooled before evaporating off the acetone under reduced pressure and the residue was taken up in ethyl acetate and poured into a 0.5M aqueous solution of hydrochloric acid and extracted with ethyl acetate. The extracts were washed with water, then successively with a saturated solution of sodium thiosulfate and a saturated aqueous solution of sodium chloride, dried and evaporated to dryness under reduced pressure to obtain 612 mg of product which was chromatographed on silica (eluant:ethyl acetate/cyclohexane 50/50) to obtain 68 mg of the desired product with a Rf=0.40 ethyl acetate/cyclohexane 50/50.

IR Spectrum: (CHCl$_3$)

| —NH—: | approx. 3400 cm$^{-1}$ |
|---|---|
| >C=O: | 1733 cm$^{-1}$ |
| | 1610 cm$^{-1}$ |

| | |
|---|---|
| Aromatic C=C's: | 1579 cm⁻¹ |
| | 1511 cm⁻¹ |
| | 1510 cm⁻¹ |
| —SO₂— | 1327 cm⁻¹ + 1141 cm⁻¹ |

STEP B: N-butyl-5-[4-[3-[benzyl-oxy]-Δ1,3,5(10)-estratrien-17β-ol-11β-yl]-phenoxy]-pentane-sulfonamide 33 mg of sodium borohydride were added under an inert gas atmosphere cooled to 0° to +5° C. to a solution of 294 mg of the product of Step A in 1.3 ml of tetrahydrofuran and 1.3 ml of methanol and the mixture was stirred for one hour at 0° to +5° C. The mixture was poured into a 1M aqueous solution of hydrochloric acid and extracted with ethyl acetate. The extracts were washed with a saturated aqueous solution of sodium chloride, dried and evaporated to dryness under reduced pressure to obtain 300 mg of product which was chromatographed on silica (eluant:ethyl acetate/cyclohexane 50/50) to obtain 194 mg of the desired product with a Rf=0.25 ethyl acetate/cyclohexane 50/50.

STEP C: N-butyl-5-[4-(Δ1,3,5(10)-estratrien-3,17β-diol-11β-yl)-phenoxy]-pentanesulfonamide 44 mg of the 10% palladium catalyst on activated charcoal were added to a solution of 194 mg of the product of Step A in 5 ml of ethyl acetate, 5 ml of ethanol and 5 ml of acetic acid and then the mixture was stirred under a hydrogen pressure of 1700 mbar for 15 minutes. The suspension was filtered, washed with a 1/1 methanol/methylene chloride mixture. The filtrate was evaporated to dryness under reduced pressure and the acetic acid was entrained with toluene. Drying was carried out under reduced pressure to obtain 172 mg of the product which was chromatographed on silica (eluant:methylene chloride/isopropanol 96/4) to obtain 142 mg of the chloride/ isopropanol 96/4) to obtain 142 mg of the desired product.

IR Spectrum: (CHCl₃)

| | |
|---|---|
| —OH: | 3601 cm⁻¹ |
| —NH—: | 3400 cm⁻¹ |
| | 1610 cm⁻¹ |
| Aromatic C=C's: | 1581 cm⁻¹ |
| | 1512 cm⁻¹ |
| —SO₂— | 1327 cm⁻¹ |
| | 1140 cm⁻¹ |

EXAMPLE 3

5-[4-(Δ1,3,5(10)-estratrien-3,17β-11β-yl)-phenoxy]-N-[dimethylamino-methylene]-pentane-sulfonamide 0.062 ml of N,N-dimethylformamide-dimethylacetal were added to a solution of 200 mg of the product of Step D of Example 1 in 1.5 ml of dimethylformamide, and the mixture was stirred for 90 minutes at ambient temperature. The reaction mixture was poured into a 1% aqueous solution of sodium hydrogen sulfate and extracted with ethyl acetate. The extracts were washed with water, then with a saturated aqueous solution of sodium chloride, dried and evaporated to dryness under reduced pressure to obtain 227 mg of product which was chromatographed on silica (eluant:methylene chloride/isopropanol 95/5) to obtain 168 mg of the desired product.

IR Spectrum: (CHCl₃)

| | |
|---|---|
| —OH: | 3602 cm⁻¹ |
| —N=CH—: | 1629 cm⁻¹ |
| | 1611 cm⁻¹ |
| Aromatic C=C's: | 1580 cm⁻¹ |
| | 1512 cm⁻¹ |

EXAMPLE 4

N-butyl-N'-[5-[4-(Δ1,3,5(10)-estratrien-3,17β-diol-11β-yl)-phenoxy]-pentylsulfonyl]-urea 20 mg of sodium hydride were added under an inert gas atmosphere to a solution of 200 mg of the product of Step D of Example 1 in 2 ml of dimethylformamide and, after 10 minutes of stirring at ambient temperature, 0.046 ml of butyl isocyanate were added. After one hour of stirring at ambient temperature, the reaction mixture was poured into a 1M aqueous solution of hydrochloric acid and extracted with ethyl acetate. The extracts were washed with a saturated aqueous solution of sodium chloride, dried and evaporated to dryness under reduced pressure to obtain 317 mg of product which was chromatographed on silica (eluant: methylene chloride/isopropanol 95/5) to obtain 146 mg of the desired product.

IR Spectrum: (nujol)

| | |
|---|---|
| OH/NH: | approx. 3360 cm⁻¹ |
| | + general absorption |
| >C=O: | 1675 cm⁻¹ |
| | 1610 cm⁻¹ |
| Aromatic C=C's: | 1577 cm⁻¹ |
| + amide → | 1540 cm⁻¹ |
| | 1510 cm⁻¹ |
| —SO₂—: | 1340 cm⁻¹ |
| | 1146 cm⁻¹ |

EXAMPLE 5

N-(4-chlorophenyl)-N-[5-[4-(Δ1,3,5(10)-estratrien-3, 17β-diol-11β-yl)-phenoxy]-pentylsulfonyl]-urea 22 mg of 50% sodium hydride were added under an inert gas atmosphere to a solution of 183 mg of the product of Step D of Example 1 in 2 ml of dimethylformamide and, after 10 minutes of stirring at ambient temperature, 73 mg of 4-chlorophenyl isocyanate were added. After 5 hours of stirring at ambient temperature, the reaction mixture was poured into a 1M aqueous solution of hydrochloric acid and extracted with ethyl acetate. The extracts were washed with a saturated aqueous solution of sodium chloride, dried and evaporated to dryness under reduced pressure to obtain 289 mg of product which was chromatographed on silica (eluant: methylene chloride/isopropanol 92.5/7.5) to obtain 86 mg of the desired product.

IR Spectrum: (nujol)

| Complex absorption OH/NH: | |
|---|---|
| >C=O: | approx. 1698 cm⁻¹ |
| | 1607 cm⁻¹ |
| Aromatic C=C's: | 1540 cm⁻¹ |
| + amide | 1511 cm⁻¹ |
| | 1494 cm⁻¹ |

EXAMPLE 6

1-[5-[4-(Δ1,3, 5(10)-estratrien-3,17β-diol-11β-yl)-phenoxy]-pentylsulfonyl]-2-imidazolidinone 20 mg of 50% sodium hydride were added under an inert gas atmosphere to a solution of 200 mg of the product of Step D of Example 1 in 2 ml of dimethylformamide and, after 10 minutes of stirring at ambient temperature, 0.035 ml of 2-chloroethylisocyanate were added. After 90 minutes of stirring at ambient temperature, the reaction medium was poured into a 1M aqueous solution of hydrochloric acid and extracted with ethyl acetate. The extracts were washed with water, then with a saturated aqueous solution of sodium chloride, dried and evaporated to dryness under reduced pressure to obtain 278 mg of product which was chromatographed on silica (eluant: ethyl acetate then methylene chloride/isopropanol 92.5/7.5) to obtain 102 mg of the desired product.

IR Spectrum: (nujol)

| General absorption OH/NH region: | |
|---|---|
| >C=O: | 1726 cm$^{-1}$ |
| | 1612 cm$^{-1}$ |
| Aromatic C=C's: | 1580 cm$^{-1}$ |
| | 1510 cm$^{-1}$ |
| | 1505 cm$^{-1}$ (shoulder) |
| —SO$_2$—: | 1155 cm$^{-1}$ |

EXAMPLE 7

N-butyl-5-[4-(Δ1,3,5 (10)-estratrien-3,17β-diol-11β-yl)-phenoxy]-N-methyl-pentanesulfonamide STEP A: N-butyl-5-[4-(Δ4,9-estradien-3,17-dione-11β-yl)-phenoxy]-N-methyl-pentanesulfonamide 362.5 mg of 11β-(4-hydroxyphenyl)-Δ4,9-estradiene-3,17-dione (Example 43 of Patent EP No. 384,842) were added under an inert gas atmosphere to a suspension of 58 mg of sodium hydride at 50% in oil in 6 ml of dimethylformamide and after stirring for 30 minutes at ambient temperature, a solution of 417 mg of the product of Preparation 2 (Stage B) in 1.5 ml of dimethylformamide was added. The temperature was allowed to rise from 23° C. to 27° C. during the introduction and then stirring was carried out for 45 minutes. The reaction mixture was poured into a 1M aqueous solution of hydrochloric acid and extracted with ethyl acetate. The extracts were washed with water then successively with a saturated solution of sodium thiosulfate and a saturated aqueous solution of sodium chloride, dried and evaporated to dryness under reduced pressure. The 883 mg of residue were chromatographed on silica (eluant: ethyl acetate/cyclohexane 60/40) to obtain 433 mg of the desired product.

IR Spectrum: (CHCl$_3$)

| >C=O in position 17: | 1735 cm$^{-1}$ |
|---|---|
| dienone | 1658 cm$^{-1}$ |
| | 1609 cm$^{-1}$ |
| C=C + | 1600 cm$^{-1}$ (shoulder) |
| Aromatic C=C's: | 1580 cm$^{-1}$ |
| | 1509 cm$^{-1}$ (strong) |
| | 1333 cm$^{-1}$ |
| —SO$_2$N<: | 1140 cm$^{-1}$ |

STEP B: N-butyl-5-[4-(Δ1,3,5(10)-estratrien-3,17β-diol-11β-yl)-phenoxy]-N-methyl-pentanesulfonamide 1) Aromatization 32 ml of acetic anhydride and 0.16 ml of acetyl bromide were added at 0° to +5° C. under an inert gas atmosphere to a solution of 404.5 mg of the product of Step A in 4 ml of methylene chloride and the mixture was stirred for 15 minutes at this temperature, then 75 minutes at ambient temperature.

2) Saponification of the acetate 0.3 ml of methanol were added to the reaction mixture cooled to 0° to +5° C., and after stirring for 10 minutes, evaporation to dryness was carried out under reduced pressure at ambient temperature. The residue was taken up in 2.4 ml of methanol and 2.4 ml of tetrahydrofuran and 0.47 ml of sodium hydroxide were added. The mixture was stirred at ambient temperature for 45 minutes.

3) Reduction of the 17-ketone 131 mg of sodium borohydride were added to the reaction mixture cooled to 0° to +5° C. and after stirring at ambient temperature for 45 minutes, the reaction mixture was poured into a 1M aqueous solution of hydrochloric acid. Extraction was carried out with ethyl acetate and the extracts were washed with water, then with a saturated solution of sodium chloride, dried and evaporated to dryness under reduced pressure. The 393 mg of residue were chromatographed on silica (eluant: ethyl acetate/cyclohexane 50/50) to obtain 193 mg of the desired product.

IR Spectrum: (CHCl$_3$)

| —OH: | 3600 cm$^{-1}$ |
|---|---|
| | 1610 cm$^{-1}$ |
| Aromatic C=C's: | 1581 cm$^{-1}$ |
| | 1512 cm$^{-1}$ |
| —SO$_2$N<: | 1332 cm$^{-1}$ |
| | 1138 cm$^{-1}$ |

EXAMPLE 8

5-[4-(Δ1,3,5(10)-estratrien-3,17β-diol-11β-yl)-phenoxy]-N-(2,2,3,3,4,4,4-heptafluorobutyl)-N-pentanesulfonamide STEP A: 5-[4-(Δ4,9-estradiene-3,17-dione-11β-yl)-phenoxy]-N-(2,2,3,3,4,4,4-heptafluorobutyl)-N-methyl-pentane-sulfonamide 40 ml of sodium hydride at 50% in oil were added to a solution of 255 mg of 11β-(4-hydroxyphenyl)-Δ4,9-estradiene-3,17-dione (Example 43 of Patent EP No. 384, 842) in 4.5 ml of dimethylformamide and after stirring for 30 minutes at ambient temperature, 400 mg of the product of Preparation 3 (Step B) were added. The mixture was stirred at ambient temperature for 45 minutes and the reaction mixture was poured into a 1M aqueous solution of hydrochloric acid and extracted with ethyl acetate. The extracts were washed successively with a saturated solution of sodium thiosulfate and a saturated aqueous solution of sodium chloride, dried and evaporated to dryness under reduced pressure. The 600 mg of residue were chromatographed on silica (eluant: ethyl acetate/essence of residue were chromatographed on silica (eluant:ethyl acetate/essence G 55/45) to obtain 335 mg of the desired product.

IR Spectrum: (CHCl$_3$)

| | |
|---|---|
| >C=O in position 17: | 1735 cm$^{-1}$ |
| dienone | 1658 cm$^{-1}$ |
| | 1609 cm$^{-1}$ |
| C=C + | 1580 cm$^{-1}$ |
| Aromatic C=C's: | 1509 cm$^{-1}$ |
| | 1342 cm$^{-1}$ |
| —SO$_2$N<: | 1148 cm$^{-1}$ |

STEP B: 5-[4-(Δ1,3,5(10)-estratrien-3,17β-diol-11β-yl)-phenoxy]-N-(2,2,3,3,4,4,4-heptafluorobutyl)-N-methyl-pentanesulfonamide 1) Aromatization 0.35 ml of acetic anhydride and 0.20 ml of acetyl bromide were added at 0° to +5° C. to a solution of 430 mg of the product of Step A in 3.5 ml of methylene chloride, and the mixture was stirred for 40 minutes at ambient temperature.

2) Saponification of the acetate 0.5 ml of methanol were added to the reaction mixture cooled to 0° to +5° C. and evaporation to dryness was carried out under reduced pressure. The residue was taken up in 3.5 ml of methanol and 0.6 ml of sodium hydroxide were added.

3) Reduction of the 17-ketone 228 mg of sodium borohydride were added to the reaction mixture and after stirring at ambient temperature for 20 minutes, acidification was carried out to pH=2 with 2N hydrochloric acid, followed by extraction with methylene chloride. The extracts were dried and evaporated to dryness under reduced pressure. The 429 mg of residue were chromatographed on silica (eluant: ethyl acetate/essence G 40/60) to obtain 266 mg of the desired product melting at 136° C.–138° C.

IR Spectrum: (CHCl$_3$)

| | |
|---|---|
| —OH: | 3615 cm$^{-1}$ |
| | 1610 cm$^{-1}$ |
| Aromatic C=C's: | 1581 cm$^{-1}$ |
| | 1512 cm$^{-1}$ |
| | 1491 cm$^{-1}$ |
| —SO$_2$N<: | 1342 cm$^{-1}$ |
| | 1148 cm$^{-1}$ |

Pharmaceutical compositions

Tablets were prepared containing 50 mg of the product of Example 7 and sufficient excipient of talc, starch, magnesium stearate for a tablet of 120 mg.

Injectable suspensions were prepared containing 25 mg of the product of Example 7 and sufficient excipient of dispersive aqueous solution: benzyl alcohol, polysorbate 80, carboxymethylcellulose (sodium salt), sodium chloride, water for injectable preparations of 1 ml.

Pharmacological study

1-Activity on the hormonal receptors using either the natural hormonal receptor of a rat (AR), or the recombinant human receptor (PR, GR and ER).

Androgen receptor of the prostate of a rat

Male Sprague Dawley EOPS rats weighing 180 to 200 g were castrated and 24 hours after the castration, the animals were sacrificed. The prostates were removed, weighed and homogenized at 0° C. using a Potter teflon-glass in a TS buffered solution (10 mM Tris, 0.25M saccharose, 2 mM DTT, 20 mM MoNa, 0.1 mM PMSF, pH 7.4) (1 g of tissue per 8 ml of TS). The homogenate was centrifuged (209,000 g for 30 minutes) at 0° C. Aliquots of the supernatant were incubated at 0° C. for 24 hours with a constant concentration (T) of tritiated testosterone in the presence of increasing concentrations, either of unlabelled testosterone (0 to 1000× 10$^{-9}$M), or of the product under test (1 to 25000×10$^{-9}$M). The concentration of bound tritiated testosterone (B) was measured in each incubate by the technique of adsorption with carbon dextran.

Human progesterone receptor

The recombinant human progesterone receptor was obtained by superexpression in an insect-Baculovirus cell system by methodology described by WEBB et al. in Journal of Methods in Cell and Molecular Biology, (1990), Vol. 2 No. 4, pp. 173–188 and whose use is described for the expression of human hormonal receptors, for example the human glucocorticoid receptor (SRINIVASAN et al. Molecular Endocrinology, (1990), Vol. 4 No. 2, pp. 209–216).

The BaculoGold Transfection Kit was used (PharMingen, reference 21000K) to insert the cDNA fragment described by KASTNER et al. (The EMBO Journal, (1990), Vol. 9 No. 5, pp. 1603–1614), containing the region coding for the human progesterone receptor and to prepare the corresponding recombinant virus. The recombinant virus was used to express the progesterone receptor in SF9 insect cells (ATCC CRL1711), by the known methodology mentioned previously.

$2 \times 10^7$ to $2.5 \times 10^7$ SF9 cells were cultivated in a 172 ml "Falcon" flask in a TNM-FH "SIGMA" medium supplemented with 10% of foetal calf serum (FCS) and with 50 micrograms/ml of gentamycin. After infection, then incubation at 27° C. for 40 to 42 hours, the cells were lysed in 1 ml of lysis buffer (1) by a freezing-defrosting cycle which was repeated twice more. The supernatant containing the recombinant human progesterone receptor was kept in liquid nitrogen in doses of 1 ml. The supernatant was diluted at the time of use according to a dilution range varying from 1/10th to 1/100th with 10 mM Tris, 0.25M saccharose, HCl buffer at pH 7.4 containing 0.1% gelatin and then was incubated at 0° C. for 24 hours with a constant concentration (T) of tritiated 17α,21-dimethyl-19-nor-Δ4,9-pregnadien-3,20-dione in the presence of increasing concentrations either of unlabelled progesterone (0–2500×10$^{-9}$M), or of unlabelled product under test (1 to 25000×10$^{-9}$M). The concentration of bound tritiated 17,21-dimethyl 19-nor-Δ4,9-pregnane-3,20-dione (B) was then measured in each incubate by the technique of adsorption with carbon dextran.

Human glucocorticoid receptor

A supernatant of SF9 cells containing the recombinant human glucocorticoid receptor was obtained by the process described above for the progesterone receptor using the cDNA fragment described HOLLENBERG et al. (Nature (1985), Vol. 318 No. 19/26, p. 635) containing the region coding for the human glucocorticoid receptor. The cells were lysed in a lysis buffer (2). The supernatant was incubated at 0° C. for 24 hours with a constant concentration (T) of 6,21-dimethyl-Δ1,4,6-pregnatrien-11β,17β-diol-20-yn-3-one tritiated in the presence of increasing concentrations either of unlabelled dexamethasone (0–1000×10$^{-9}$M), or of the unlabelled product under test (1 to 25000×10$^{-9}$M). The concentration of bound tritiated 6,21-dimethyl-Δ1,4,6-pregnatrien-11β,17β-diol-20-yn-3-one (B) was then measured in each incubate by the technique of adsorption with carbon dextran.

Human estrogen receptor

A supernatant of SF9 cells containing the recombinant human estrogen receptor was obtained by the process described above for the progesterone receptor using the cDNA fragment described in the HEGO expression vector by TORA et al. (EMBO Journal (1989), Vol. 8 No. 7, pp. 1981–1986), containing the region coding for the human estrogen receptor of "wild type" with a glycine in position 400. The cells were lysed in the lysis buffer (1). The supernatant was incubated at 0° C. for 24 hours with a constant concentration (T) of tritiated estradiol in the presence of increasing concentrations either of unlabelled estradiol ($0-1000\times10^{-9}M$), or of the unlabelled product under test ($1$ to $25000\times10^{-9}M$). The concentration of bound tritiated estradiol (B) was then measured in each incubate by the technique of adsorption with carbon dextran.

Expression of the results and methods of calculation
Calculation of the relative bond affinity (RBA).

The following 2 curves were traced: percentage of bound tritiated hormone B/BO as a function of the logarithm of the concentration of unlabelled reference hormone or as a function of the logarithm of the concentration of the unlabelled product under test.

The straight line of the following equation was determined:

$$I_{50}=100(BO/BO+Bmin/BO)/2 \text{ i.e. } I_{50}=100(1+Bmin/BO)/2=50(1+Bmin/BO)$$

BO=Concentration of bound tritiated hormone in the absence of any unlabelled product, B=Concentration of bound tritiated hormone in the presence of a concentration X of unlabelled product, B min=Concentration of bound tritiated hormone in the presence of a large excess of cold reference hormone (500 nM), The intersections of the straight line $I_{50}$ and the curves allowed the evaluation of the concentrations of unlabelled reference hormone (CH) and of the unlabelled product under test (CX) which inhibited by 50% the specific binding of the tritiated hormone on the receptor.

The relative bond affinity (RBA) of the product under test was determined by the equation:

$$RBA=100(CH/CX)$$

The RBA's of the reference products estradiol, progesterone, dexamethasone and testosterone were arbitrarily taken to be equal to 100. The results of the RBA's obtained were the following:

| Products of Example | hER Estradiol = 100 | hGR Dexamethasone = 100 | hPR Progesterone = 100 | AR Testosterone = 100 |
|---|---|---|---|---|
| 2 | 21 | 82 | 37 | 3 |
| 7 | 4 | 152 | 111 | 2.5 |
| 8 | 19 | 114 | 55 | 1.5 |

CONCLUSION

The products studied, particularly the products of Examples 2 and 8, have a marked affinity for the estrogen receptor. The products of Examples 2, 7 and 8 have a marked affinity for the glucocorticoid and progesterone receptors.

Lysis buffers: (1) Tris-HCl pH 8: 20 mM, EDTA: 0.5 mM, DTT: 2 mM, glycerol: 20%, KCl: 400 mM, PIC 1°/oo.

(2) Potassium phosphate pH 7.0: 50 mM, DTT: 5 mM, glycerol: 20%, Sodium molybdate: 20 mM, PIC 1°/oo.

PIC: leupeptin, pepstatin A, aprotinin, antipaine, chymostatin. Final concentration of each one: 2.5 ug/ml 2-Anti-proliferative activity on the growth of MCF-7 human breast tumour cells

DESCRIPTION OF THE TEST a) Cell culture

The MCF-7 lines were maintained in culture in a base medium (according to 1) containing 5% of foetal calf serum at 37° C. under a humid atmosphere containing 5% $CO_2$. The subconfluent cells were collected by trypsination (0.1% trypsin, 0.02% EDTA) and then rinsed by gentle centrifuging. A sample of the cells in suspension was counted with a Malassez cell.

b) Study of the growth

The cells were resuspended in a base medium without phenol red in the presence of 5% of steroid-free FCS, and stimulated either by 0.1 nM of estradiol, or by 10 ng/ml of EGF+1 ng/ml of PDGF. The cells were seeded at a rate of 50,000 cells per well in multi-well plates (24 wells of 2.5 $cm^2$). Twenty-four hours after the seeding (DO), the product to be tested was added to the mixture in ethanolic solution (final concentration of ethanol: 0.1%), at a concentration of $10^{-11}$ to $10^{-6}M$, the control wells receiving the same concentration of ethanol. The media containing the products were renewed every 48 hours. At the end of the experiment (D7 to D9), the mixture was extracted and the cells were immediately fixed with 250 microliters of methanol to dose the DNA. The anti-proliferative activity of the products was evaluated by their capacity to inhibit the increase of DNA relative to the control.

c) DNA dosage

The DNA was dosed by a fluorimetric method using DABA (3,5-diaminobenzoic acid) (according to 2): 200 microliters of DABA were added to each well and the plates were incubated for 45 minutes at 56° C. Then, 2 ml of 1N HCl were added and the fluorescence was measured using a fluorimeter (excitation wavelength: 408 nm, emission wavelength: 510 nm). The quantity of DNA per well was evaluated relative to a reference scale obtained by treating a calf thymus DNA standard under the same conditions.

Results

The concentration in nM which inhibited by 50% the growth of the MCF-7 cells stimulated by EGF+PDGF ($IC_{50}$) was determined in the manner indicated above.

Results:

Product of Example 2: $IC_{50}$=0.016 nM

Product of Example 7: $IC_{50}$=0.015 nM

Product of Example 8: $IC_{50}$=0.026 nM (1) A base medium was prepared as follows:

MEM medium (Minimal Essential Medium) to which were added:

1% non-essential amino acids (GIBCO), peni-strepto (100 U/ml penicillin, 0.1 mg/ml streptomycin), 0.1% fungizone, 2 mM glutamine, 2.25 mg/ml sodium bicarbonate.

(2) Puzas and Goodman, Analytical Biochemistry, Vol. 86, p. 50, 1978.

Various modifications of the compounds and method of the invention may be made without departing from the spirit or scope thereof and it is to be understood that the invention is intended to be limited only as defined in the appended claims.

What we claim is:

1. A compound of the formula selected from the group consisting of

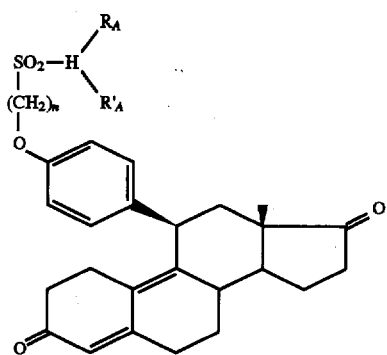

IV

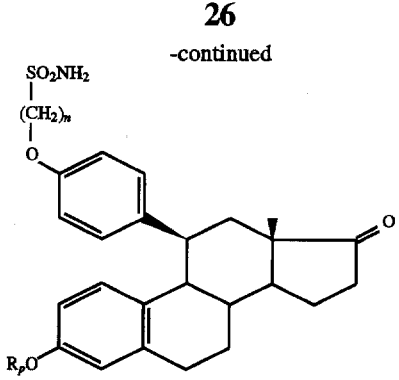

VI

-continued wherein $R_p$ is a protective group, $R_A$ and $R'_A$ are individually selected from the group consisting of hydrogen, optionally substituted alkyl, acyl of an organic carboxylic acid of up to 12 carbon atoms and optionally substituted aryl and aralkyl with at least one of $R_A$ and $R'_A$ not being hydrogen or together with the nitrogen atom to which they are attached form a saturated heterocycle of 5 to 6 ring members optionally containing another heteroatom selected from the group consisting of nitrogen, oxygen and sulfur and optionally substituted with an alkyl and n is an integer from 1 to 7.

* * * * *